(12) United States Patent
Christopher et al.

(10) Patent No.: US 7,771,652 B2
(45) Date of Patent: Aug. 10, 2010

(54) COMBINED USE OF AN ALKALINE EARTH METAL COMPOUND AND A STERILIZING AGENT TO MAINTAIN OSTEOINDUCTION PROPERTIES OF A DEMINERALIZED BONE MATRIX

(75) Inventors: Renee A. Christopher, Dryden, NY (US); J. Anastasia Nichols, Ithaca, NY (US)

(73) Assignee: Novasterilis, Inc., Lansing, NY (US)

( * ) Notice: Subject to any disclaimer, the term of this patent is extended or adjusted under 35 U.S.C. 154(b) by 214 days.

(21) Appl. No.: 12/101,489

(22) Filed: Apr. 11, 2008

(65) Prior Publication Data

US 2009/0257914 A1     Oct. 15, 2009

(51) Int. Cl.
*A61L 2/20* (2006.01)

(52) U.S. Cl. .................................................. 422/33

(58) Field of Classification Search ................ 422/28, 422/31, 33
See application file for complete search history.

(56) References Cited

U.S. PATENT DOCUMENTS 7,108,832 B2 *    9/2006    Christensen et al. ........... 422/33

* cited by examiner

*Primary Examiner*—Walter D Griffin
*Assistant Examiner*—Timothy Cleveland
(74) *Attorney, Agent, or Firm*—Welsh & Flaxman LLC

(57) ABSTRACT

A method is disclosed that produces allografts from matrices typically containing demineralized bone matrix (DBM) powder, demineralized bone matrix gel, demineralized bone matrix paste, bone cement, cancellous bone, or cortical bone and mixtures thereof. The matrices are sterilized utilizing supercritical $CO_2$ in the presence of a sterilizing additive and an entrainer such as an alkaline earth metal compound, preferably $CaCO_3$. The resultant allograft materials have a reduced rate of rejection when used in allograft procedures including, bone, cartilage, tendon, and ligament grafting procedures.

10 Claims, 2 Drawing Sheets

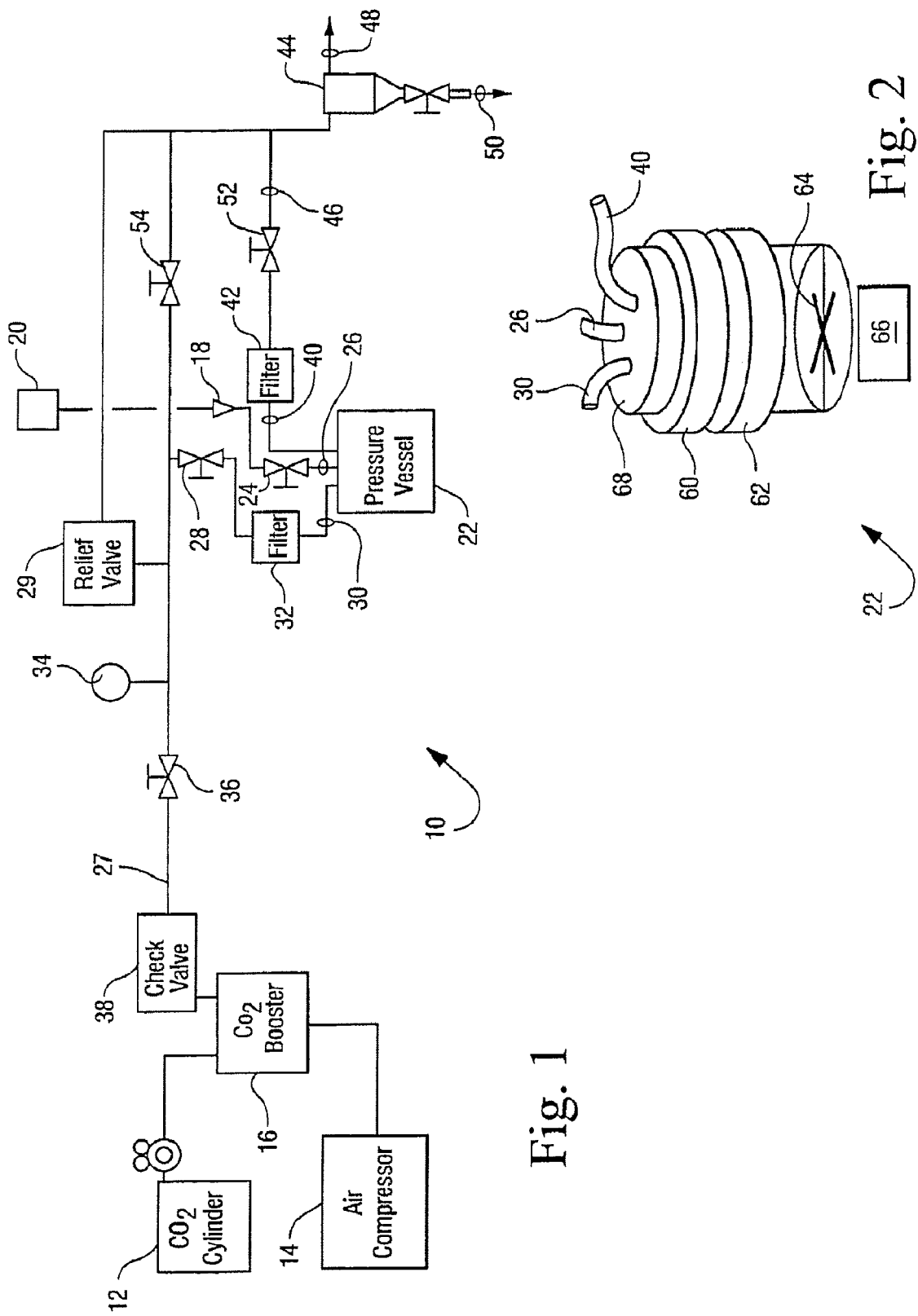

US 7,771,652 B2

COMBINED USE OF AN ALKALINE EARTH METAL COMPOUND AND A STERILIZING AGENT TO MAINTAIN OSTEOINDUCTION PROPERTIES OF A DEMINERALIZED BONE MATRIX

FIELD OF THE INVENTION

The present invention relates to methods of reducing rejection in allograft procedures including, bone, cartilage, tendon, and ligament grafting procedures.

BACKGROUND OF THE INVENTION

Allograft bone is a graft substitute readily available from cadavers and avoids the surgical complications and subject morbidity associated with harvesting autologous bone. Allograft bone is essentially a load-bearing matrix comprised of cross-linked collagen, hydroxyapatite, and osteoinductive Bone Morphogenetic Proteins (BMP). Human allograft tissue is widely used in orthopedic surgery. Allograft tissue is strong, integrates with the recipient host bone, and can be shaped either by the surgeon to fit the specific defect or shaped commercially by a manufacturing process. Allograft bone is available in two basic forms: cancellous and cortical. Cortical bone is a highly dense structure comprised of triple helix strands of collagen fiber reinforced with hydroxyapatite. The hydroxyapatite component is responsible for the high compressive strength and stiffness of bone while the collagen fiber component contributes to its elastic nature, as well as torsional, shear, and tensile strength. Cortical bone is the main load-bearing component of long bones in the human body.

Use of allograft material is often a preferred treatment option for musculoskeletal related injuries. Significant problems associated with the use of allografts are recipient rejection of the tissue due to the presence of donor related antigens still present in the allograft, allograft inability to incorporate into the host, and contaminated tissue used in transplant. Numerous methodologies have been employed to reduce the level of antigenic compounds present in allografts and perform low-level disinfection and sterilization. These methods generally include numerous washes with a variety of chemicals. These methods have extreme drawbacks to the extent that they utilize reactive chemicals that alter the structural components of the allograft or denature and/or remove compounds that facilitate integration of the allograft by the recipient.

It therefore would be highly desirable if a sterilization method could be provided leading to improved clincal outcomes of bone grafting.

Recently, in U.S. Pat. No. 6,149,864 to Dillow et al and U.S. Pat. No. 7,108,832 to Christensen et al. (the entire content of both are expressly incorporated herein by reference), the use of supercritical $CO_2$ was disclosed as an alternative to existing technologies for sterilizing a wide range of products for the healthcare industry with little or no adverse effects on the material treated.

SUMMARY OF THE INVENTION

The present invention fills the foregoing need by providing devices, systems and methods for repairing bone and soft tissue defects in a subject, wherein the bone and soft tissue defects are repairable by a bone or soft tissue graft procedure. The present invention contemplates the use of allografts that have been produced from matrices typically containing demineralized bone matrix (DBM) powder, demineralized bone matrix gel, demineralized bone matrix paste, bone cement, cancellous bone or cortical bone sterilized utilizing supercritical $CO_2$ in the presence of a sterilizing additive and an alkaline earth metal compound such as $CaCO_3$.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIG. 1 is a schematic view of a presently preferred sterilization apparatus in accordance with the present invention;

FIG. 2 is a detailed schematic view of the pressure vessel employed in the apparatus of FIG. 1.

DETAILED DESCRIPTION OF THE INVENTION

Figure 3:
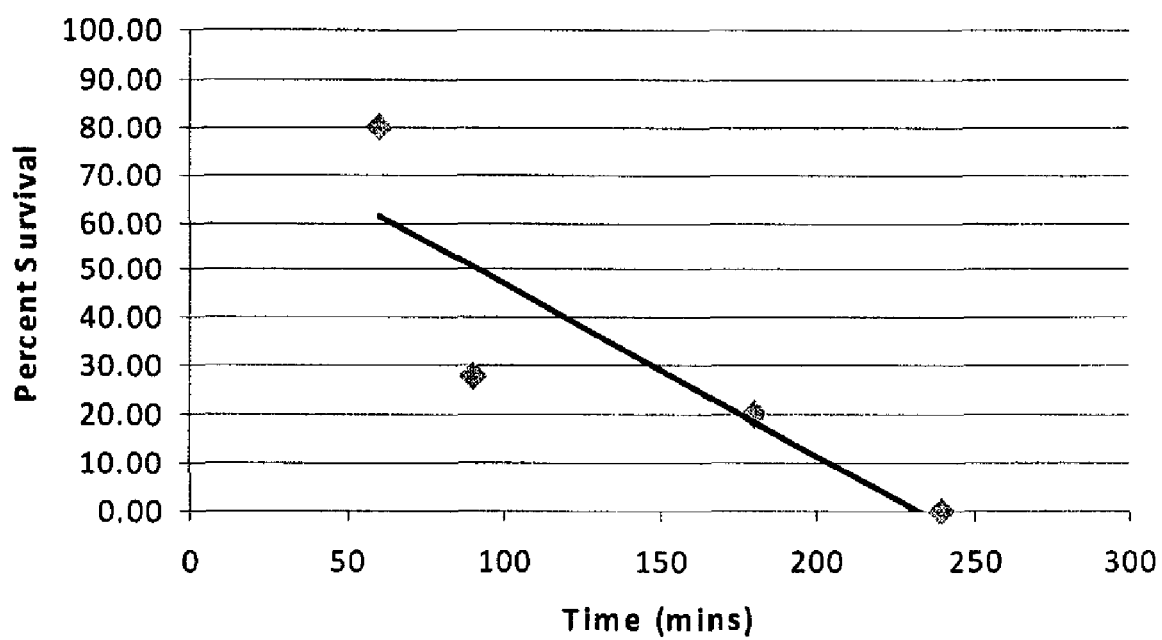
FIG. 3 is a graph that relates the survival percentage of endospores to processing time in the apparatus of FIG. 1.

The present invention contemplates the production of allografts from matrices typically containing one or more material of: demineralized bone matrix (DBM) powder, demineralized bone matrix gel, demineralized bone matrix paste, bone cement, cancerous bone, cortical bone, or mixtures thereof and the like; that are sterilized utilizing supercritical $CO_2$ in the presence of a sterilizing additive and an entrainer such as an alkaline earth metal compound, preferably $CaCO_3$. The resultant allograft materials display a reduced rate of rejection when used in bone allograft. The sterilization apparatus and methods of the present invention are usefully employed to sterilize a variety of materials to produce allografts including but not limited to demineralized bone matrix powder, demineralized bone matrix gel, demineralized bone matrix paste, bone cement, cancellous bone and cortical bone and the like. The instant invention can be practiced with different bone structures. For example, suitable bone graft structures may include cartilage, cortical bone, cancellous bone, subchondral bone, and any combination of the various bone tissue types. In addition, bone-tendon-bone allografts used for ACL reconstruction and structures employed for long bone allograft tumor reconstruction can also be used. The graft structure may comprise a composite bone that includes a polymer and a demineralized bone, and, optionally, a bone powder. These compounds may be used in different ratios that can be determined by a person of ordinary skill in the art. A non-limiting example of the suitable composite bone includes 50% polylactide (PLA), 30% demineralized bone (<80 micron), and 20% bone particles (<80 micron).

The sterilization apparatus and methods of the present invention preferably use carbon dioxide at or near its supercritical pressures and temperature conditions as a sterilant. Thus, the sterilization process of the present invention is practiced using carbon dioxide as a sterilant at pressures between about 1000 to about 3500 psi, at temperatures in the range between about 25° C. to about 60° C. Most preferably, the article to be sterilized is subject to carbon dioxide at or near such pressure and temperature conditions for times ranging from about 20 minutes to about 12 hours. The carbon dioxide employed in the practice of the present invention is most preferably substantially pure. Thus, trace amounts of other gases may be tolerated provided that the sterilization properties of the carbon dioxide are not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

The chemical sterilizing additives employed in the present invention include peroxides, carboxylic acids, carbonic anhydrase and mixtures thereof. Preferred carboxylic acids include alkanecarboxylic acids and/or alkanepercarboxylic acids, each of which may optionally be substituted at the alpha carbon with one or more electron-withdrawing substituents, such as halogen, oxygen and nitrogen groups. Particularly preferred species of chemical sterilizing additives employed in the practice of the present invention include hydrogen peroxide ($H_2O_2$) acetic acid (AcA), peracetic acid (PAA), carbonic anhydrase, trifluoroacetic acid (TFA), and mixtures thereof.

The chemical sterilization additive is employed in a sterilization enhancing effective amount of at least about 0.0001 vol. % and greater, based on the total volume of the carbon dioxide. The amount of sterilization additive will be dependent upon the particular sterilization additive that is employed. Thus, for example, carbonic anhydrase may be present in relatively small amounts of about 0.0001 vol. % and greater, peracetic acid in small amounts 0.0001 vol. % and greater, while acetic acid may need to be employed in amount of about 0.001 vol. % and greater. Thus, a range of at least about 0.0001 vol. % and greater, up to about 2.0 vol. % will typically be needed in order to achieve a sterilization enhancing effect in combination with carbon dioxide.

The entrainer is a compound such as an alkaline earth metal compound, preferably calcium carbonate ($CaCO_3$), capable of disassociating into an alkaline earth metal ion during the sterilization treatment. During a sterilization run, the extra calcium supplied by the entrainer is released and forms a reaction with the chemical sterilization additive, creating the formation of calcium peroxides.

$$CaO_2 + 2H^+ \leftrightarrow H_2O_2 + Ca^{2+}$$

$$CO_2(s) + H_2O + Ca^{2+} \leftarrow CaCO_3 + 2H^+$$

$$CaO_2 + CO_2 + H_2O \leftrightarrow CaCO_3 H_2O_2$$

$$CaCO_3 \leftrightarrow Ca^{2+} CO_3^{2-}$$

The use of supercritical $CO_2$ allows for terminal sterilization of the allograft tissue. The addition of an entrainer such as $CaCO_3$ maintains the structural integrity, proteins and other molecules necessary for osteoinduction and incorporation of graft into host. It has been determined that the combined use of the sterilizing additive with the entrainer in the present sterilization process improves the ability of the formed allograft to be accepted by the recipient.

The amount of entrainer will be dependent upon the particular bone matrix materials and amounts thereof employed in making of the final allograft. The entrainer improves the osteoinduction properties of the graft into the host. The amount of entrainer is not based upon bone weight, but is actually concentration based and employed in an integration facilitating amount ranging from about 1 mil Moles (mM) to 100 mM, preferably at least 1 mM to 10 mM, when added in aqueous solution.

It has been observed that 6-log reductions in CFUs may be achieved in accordance with the present invention by subjecting materials to be sterilized under sterilization temperature and pressure conditions using an additive-containing supercritical carbon dioxide as a sterilant fluid, wherein the additive is carbonic anhydrase. Further, this process is enhanced where the sterilant fluid is agitated during the sterilization process.

One presently preferred embodiment of an apparatus 10 according to the present invention is depicted in accompanying FIGS. 1 and 2. In this regard, it can be seen that the apparatus includes a standard compressed gas cylinder 12 containing carbon dioxide, and a standard air compressor 14 used in operative association with a carbon dioxide booster 16 (e.g., Haskel Booster AGT 7/30). Alternatively, the air compressor 14 and booster 16 can be replaced with a single carbon dioxide compressor.

An additive cycle is also provided by means of a series of an inlet port 18 that allows additive contained in reservoir 20 to be added to a pressure vessel 22 through valve 24 and additive line 26. Alternatively, the sterilizing additive, such as carbonic anhydrase alone or mixed with water, can be introduced by soaking it into an absorbent pad and placing the pad in the reactor pressure vessel 22 along with the bone matrix material and entrainer to be treated. These bone matrix materials are preferably placed in a bag that is microporous, enabling the sterilizing fluid to pass through the pores of the bag to directly contact with the bone matrix and entrainer materials. The carbon dioxide is introduced to the reactor pressure vessel 22 from header line 27 via valve and regulator (herein called valve 28) and $CO_2$ supply line 30. The bone matrix materials or samples remain in contact with the supercritical fluid until such time when sterilization has occurred and the entrainer or alkaline earth metal compound has disassociated and combined with the sterilization agent to add sufficient calcium or other desired ion into the bone matrix being treated so as to facilitate integration of the produced allograft into a recipient.

A filter 32 (e.g., a 0.5 micron filter) is provided in the supply line 30 to prevent escape of material from the vessel. A pressure gauge 34 is provided downstream of $CO_2$ shut-off valve 36 in supply header 27 to allow the pressure to be visually monitored. A check valve 38 is provided in the line 27 upstream of the valve 36 to prevent reverse fluid flow into the booster 16. In order to prevent an overpressure condition existing in line 27, a pressure relief valve 9 may be provided.

An outlet line 40 through valve and regulator (herein called valve 52) allows the reactor pressure vessel 22 to be depressurized. In this regard, the depressurized fluid exits the reactor pressure vessel 22 via outline line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components.

The reactor pressure vessel 22 is most preferably constructed of stainless steel (e.g., 316 gauge stainless steel) and has a total internal volume sufficient to accommodate the materials being sterilized either on a laboratory or commercial scale. For example, in laboratory studies, an internal volume of 600 mL (e.g., approximately 8 inches long by about 2.5 inches inside diameter) was deemed adequate As is perhaps more clearly shown in FIG. 2, the reactor pressure vessel 22 includes a vibrator 60, a temperature control unit 62, and a mechanical stirring system most preferably comprised of an stirring impeller 64 and a magnetic driver 66. The reactor pressure vessel 22 contains a conventional basket (not shown) that is also preferably constructed of 316 gauge stainless steel. The basket serves to hold the items to be sterilized as well as to protect the stirring impeller 64 and direct the sterilant fluid in a predetermined manner.

The reactor pressure vessel 22 may be operated at a constant pressure or under continual pressurization and depressurization (pressure cycling) conditions without material losses due to splashing or turbulence, and without contamination of pressure lines via back diffusion. The valves 24, 28 and 52 allow the reactor pressure vessel 22 to be isolated and removed easily from the other components of the apparatus 10. The top 68 of the reactor pressure vessel 22 may be removed when depressurized to allow access to the vessel's interior.

In use, the material to be sterilized is introduced into the interior space of the reactor pressure vessel 22 along with any initial portion of liquid sterilization additive from reservoir 20 or an additive pad. The temperature control unit 62 is operated so as to set the desired initial temperature for sterilization. The reactor pressure vessel 22 may then be pre-equilibrated with carbon dioxide from gas cylinder 12 at atmospheric pressure, following which the magnetic driver 66 is operated so as to activate the stirring impeller 64. The reactor pressure vessel 22 may thereafter be pressurized to a desired pressure by introducing additional carbon dioxide gas from gas cylinder 12 via the air compressor 14 linked to carbon dioxide booster 16.

In order to affect a pressure cycling of the reactor pressure vessel 22, an amount of carbon dioxide may be released therefrom via depressurization outline line 40 by momentarily opening valve 52 sufficient to partially reduce pressure within the reactor pressure vessel 22. Additive may be introduced into the reactor pressure vessel 22 for any given pressure cycle by opening valve 24 which allows liquid additive to flow from reservoir 20 into inlet port 18. It will be understood that the sterilization additives may be introduced prior to pressurization and/or during pressure cycling. Prior to pressurization, additives are introduced directly into the reactor pressure vessel 22 prior to sealing and/or via the additive port 18. The sterilization additives are most preferably introduced during the cycling stages by measured addition to the additive port 18 at ambient pressures. The port 18 is subsequently sealed and the additive chamber is pressurized so that the additive may enter the reactor pressure vessel 22 without altering the internal pressure. The exact mechanism of addition may be modified such that the process is more efficient and/or convenient.

Following additive introduction, the reactor pressure vessel 22 may be repressurized to a desired pressure following introduction of the liquid additive therein. Such depressurization/repressurization with introduction of liquid additive may be repeated for any number of cycles that may be desired. The cycle of depressurization and repressurization as well as the introduction of the carbon dioxide and liquid additive may be automatically controlled via a controller screen which sequences the various valves discussed previously so as to achieve the desired pressure conditions and cycles.

Most preferably, periodic agitation to the contents of vessel 22 is effected using vibrator 60 through the entire process. Intermittent or continuous agitation of the reactor vessel and its contents is performed by vibrating the reactor vessel during sterilization. Agitation enhances mass transfer of the carbon dioxide and additives by eliminating voids in the fluid such that the material being sterilized comes into more complete contact with sterilant. The specific means of agitation may be adjusted to accommodate the particular apparatus employed and to optimize sterilization times, temperatures, and pressure cycles. When sterilization is complete, the vessel 22 is depressurized, the magnetic drive 66 is stopped thereby stopping the stirring impeller 64, and the thus sterilized material removed by opening top 68 of vessel 22.

It is theorized that, in conjunction with near-critical or supercritical carbon dioxide, the chemical sterilization additives employed in the present invention likely enhance sterilization by increasing the acidity of the interior of the bacterial cell, especially in the presence of water. Moreover, additives may enhance the permeability of the cell to carbon dioxide, irreversibly inhibit essential cellular processes, and/or extract components required for cell viability, all of which could possibly contribute to enhancements in sterilization that have been observed.

The present invention will be further understood after careful consideration is given to the following examples which are not intended to limit the scope of the present invention.

EXAMPLE 1

The reactor vessel 22 was opened and in each of ten porous Mylar bags in a basket were placed 0.05 g of demineralized bone matrix (DBM) powder (allograft bone material) to be sterilized by the process of the present invention. A standard additive pad was cut in half and 0.0009 vol. % of peracetic acid base additive (4/1 by volume of a peracetic acid/ $H_2O_2$ mixture) was placed on the left half pad and 2.5 ml of an aqueous solution of $CaCO_3$ (1 mM) was placed on the right half pad. The reactor vessel was closed and programmed to run for 4 hours at the standard parameters (1436 psi, 700 rpm, 33° C.). The 700 rpm is the speed at which the basket is agitated during processing. The reactor vessel was charged with $CO_2$. The reactor vessel was activated and the following occurred: 1) pressurization to supercritical $CO_2$ conditions in 5-15 minutes; 2) the process ran for varying times between 50 and 240 minutes at the above parameters; and then 3) depressurization occurred for 12-25 minutes to 0 psi. After depressurization the lid was opened, the baskets were removed and the samples were retrieved and tested for the presence of endospores (percent survival of endospores). Fraction negative testing was performed on three or four groups of ten samples for each plotted time interval of testing, and the results are shown in FIG. 3. The testing procedure demonstrated the ability to achieve linearity of kill of endospores on demineralized bone matrix products using the above process parameters.

EXAMPLE 2

Nine separate samples, each containing one gram of demineralized bone matrix (DBM) powder, were treated in Tyvek packaging with 0.0009 vol. % of a peracetic acid/ $H_2O_2$ mixture(4/1 by volume mixture) according to the procedures of Example 1. Additionally nine separate samples, each containing one gram of demineralized bone matrix (DBM) powder, were evaluated in Tyvek packaging that contained both the same amount of peracetic acid/ $H_2O_2$ and 5 ml of 10 mM of $CaCO_3$. The weight of each of the 18 samples was recorded before and after being subjected to sterilization runs. The average weight change of the initial nine samples that contained no additional $CaCO_3$ was a loss of 0.0055 grams per sample as displayed in Table 1. The average weight change of the nine samples that were treated with additional $CaCO_3$ was a loss of 0.001 grams per sample as displayed in Table 1. These results suggest that the addition of $CaCO_3$ to the system stabilizes the loss of weight of the bone mass which could be representative of loss of calcium.

TABLE 1

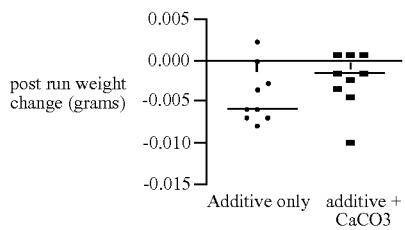

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the present invention.

What is claimed is:

1. A sterilization method for a bone matrix for use as an allograft to facilitate integration of the allograft into a recipient comprising: (a) bringing a material used in the formation of a bone matrix in need of sterilization into contact with: (1) a sterilant fluid comprised of carbon dioxide at or near its supercritical pressure and temperature conditions, (2) a chemical sterilization additive and (3) an entrainer capable of disassociating into alkaline earth metal ions; and (b) maintaining contact between the material with the sterilant fluid under said temperature and pressure conditions for a time sufficient to achieve sterilization and impregnation of the disassociated entrainer into the bone matrix.

2. The sterilization method of claim 1, wherein the entrainer is an alkaline earth metal compound used in an integration facilitating amount ranging from about 1 mM to 100 mM in an aqueous solution.

3. The sterilization method of claim 2, wherein the alkaline earth metal compound is a calcium compound.

4. The sterilization method of claim 2, wherein the alkaline earth metal compound is calcium carbonate.

5. The sterilization method of claim 1, wherein the material to be treated includes thermally or hydrolytically sensitive tissue for implantation or transplantation that have been produced from matrices selected from the group comprising: demineralized bone matrix (DBM) powder, demineralized bone matrix gel, demineralized bone matrix paste, bone cement, cancellous bone, cortical bone and mixtures thereof.

6. The sterilization method of claim 1, wherein the chemical sterilization additive is present in an amount of between about 0.0001% to about 2.0% based on the total volume of the sterilant fluid.

7. The sterilization method of claim 1, wherein the chemical sterilization additive comprises a mixture of carbonic anhydrase and peracetic acid.

8. The sterilization method of claim 1, wherein the chemical sterilization additive comprises a mixture of carbonic anhydrase and a carboxylic acid.

9. The sterilization method of claim 1, wherein the chemical sterilization additive comprises a mixture of acetic acid, hydrogen peroxide and peracetic acid.

10. The sterilization method of claim 1, wherein the chemical sterilization additive comprises a mixture of hydrogen peroxide and peracetic acid.

* * * * *